United States Patent

Haber et al.

[11] Patent Number: 5,507,730
[45] Date of Patent: Apr. 16, 1996

[54] ONE-PIECE GLASS PREFILLED SYRINGE SYSTEM

[75] Inventors: Terry M. Haber, El Toro; William H. Smedley, Lake Elsinore; Clark B. Foster, Laguna Niguel, all of Calif.

[73] Assignee: Habley Medical Technology Corporation, Laguna Hills, Calif.

[21] Appl. No.: 317,856

[22] Filed: Oct. 4, 1994

[51] Int. Cl.$^6$ .................................................. A61M 5/00
[52] U.S. Cl. ........................... 604/187; 604/223; 604/233
[58] Field of Search .................................... 604/110, 187, 604/192, 223, 233; 128/919

[56] References Cited

U.S. PATENT DOCUMENTS

| | | | |
|---|---|---|---|
| 4,875,896 | 10/1989 | Kurtz | 604/187 |
| 5,135,507 | 8/1992 | Haber et al. | 604/187 |
| 5,197,954 | 3/1993 | Cameron | 604/110 |

*Primary Examiner*—John D. Yasko
*Attorney, Agent, or Firm*—Hawes & Fischer

[57] ABSTRACT

A one-piece disposable syringe system is disclosed including a conventional syringe having a glass barrel that is prefilled with a measured dose of pharmaceutical and a syringe support and disposal jacket that is adapted to hold the syringe in an injection mode to facilitate the administration of an injection of the pharmaceutical from the barrel and surround the syringe in a disposal mode to form a compact package and thereby facilitate the safe handling and disposal of the syringe while avoiding an accidental needle stick and the possible spread of contagious disease. The syringe support and disposal jacket has lower and upper body members that are rotatably connected together by an integral living hinge. The syringe is coupled to the support and disposal jacket and rotatable from a first position in the injection mode where the upper and lower body members are spaced from one another to a second position in the disposal mode where the lower and upper body members are moved atop one another and locked together with the syringe shielded therebetween.

15 Claims, 3 Drawing Sheets

ONE-PIECE GLASS PREFILLED SYRINGE SYSTEM

BACKGROUND OF THE INVENTION

1. Field of the Invention.

This invention relates to a one-piece syringe system including a prefilled glass barrel and a syringe support and disposal jacket by which the injection of a liquid pharmaceutical may be administered and a compact package formed at the conclusion of the injection with the needle cannula destroyed and the barrel surrounded by the jacket to permit the safe handling and disposal of the syringe.

2. Background of the Invention

There is a growing need for a low cost, single use syringe system that is capable of permitting large population centers to be inoculated with a pre-measured dose of fluid medication. This need is particularly critical in third world and developing countries. To meet this objective, it would be desirable that the syringe system be disposable and non-reusable to prevent the proliferation of drug abuse. Moreover, the syringe system should be associated with a compact and integral disposal package to minimize the volume of potentially hazardous waste and to permit the system to be safely handled by health care workers while avoiding an accidental needle stick and the possible spread of contagious disease.

One example of a compact and disposable one-piece syringe system is available by referring to U.S. Pat, No. 5,135,507 issued Aug. 4, 1992 to Terry M. Haber et al.

SUMMARY OF THE INVENTION

This invention relates to a one-piece syringe system including a conventional syringe having a glass barrel that is prefilled with a measured dose of liquid pharmaceutical and a syringe support and disposal jacket that is adapted to either support the syringe in an injection mode to facilitate the administration of an injection of the pharmaceutical or surround the syringe in a disposal mode to form a compact package that is suitable to facilitate the safe handling and disposal of the syringe. The syringe includes the usual plunger stem having a plunger flange at one end thereof that receives an axial pushing force and a plunger at the opposite end that moves distally through the barrel in response to the axial pushing force so as to expulse the pharmaceutical via a needle cannula. The syringe support and disposal jacket has a lower body member and an upper body member that are rotatably joined together at an integral living hinge. Each of the lower and upper body members has a longitudinally extending recess and a plunger snap-in slot. The lower body member has a cavity formed therethrough and a barrel carrier rotatable within the cavity and coupled to the barrel of the syringe. A pair of locking tabs extend from opposite sides of the lower body member, and a pair of locking notches are formed in opposite sides of the upper body member for receipt of the locking tabs when the syringe support and disposal jacket is in the disposal mode. A plunger flange receptacle is formed in the upper body member to receive the plunger flange of the syringe when the syringe is in the injection mode.

In operation, the one-piece syringe system is removed from its shipping and storage package and moved to the injection mode by rotating the syringe support and disposal jacket around its integral hinge so that the lower and upper body members thereof form an angle of approximately 60 degrees. Next, the barrel carrier is rotated in the cavity through the lower body member until the barrel of the syringe that is coupled to the carrier extends through the cavity in transverse alignment with the lower body member. Then, the plunger flange of the syringe is located in the plunger flange receptacle at the upper body member. To administer an injection, the upper body member of the syringe support and disposal jacket is pushed towards the lower body member to cause the plunger stem and the plunger connected thereto to move distally through the barrel of the syringe. Hence, the pharmaceutical is expulsed from the barrel to a target tissue area via the needle cannula.

At the conclusion of the injection, the one-piece syringe system is moved to the disposal mode by first rotating the barrel carrier in the cavity through the lower body member of the syringe support and disposal jacket until the barrel coupled to the carrier is rotated into the longitudinal recess in the lower body member. Next, the lower and upper body members of the syringe support and disposal jacket are rotated around the integral hinge therebetween and into face-to-face alignment one atop the other. Accordingly, the longitudinal recesses of the lower and upper body members surround and enclose the barrel of the syringe. Moreover, the plunger lock-in slots of the lower and upper body members surround the plunger flange of the syringe to immobilize the plunger. What is more, the locking tabs of the lower body member are received within respective locking notches of the upper body member to lock the lower and upper body members together with the syringe shielded therebetween to form a compact disposable package that is safe for handling and disposal while avoiding an accidental needle stick. During the rotation of the syringe support and disposal jacket, the needle cannula is bent by the integral hinge so as to prevent reuse and the possible proliferation of drug abuse.

DETAILED DESCRIPTION

Figure 1:
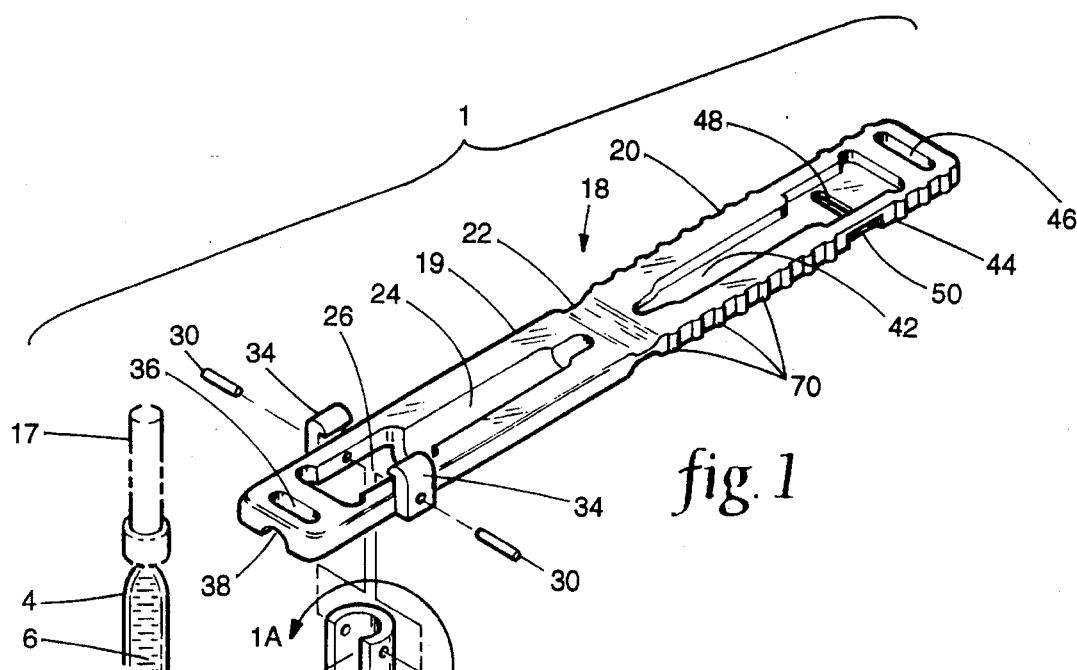
FIG. 1 is an exploded view showing a conventional syringe coupled to a syringe support and disposal jacket to form the one-piece glass prefilled syringe system of the present invention.

The one-piece prefilled syringe system 1 which forms the present invention is initially described in detail while referring to FIG. 1 of the drawings. The system 1 to be described below includes a conventional, single use, disposable syringe 2 having a glass barrel 4 that is prefilled with a measured dose of liquid pharmaceutical 6. A hypodermic needle cannula (designated 8 in FIGS. 2 and 3) communicates fluidically with the pharmaceutical 6 at the distal end of the barrel 4, and a plunger 10 is disposed at the proximal end of the barrel and adapted to slide distally therethrough so as to cause the pharmaceutical 6 to be expulsed by way of the needle cannula. The syringe 1 includes the usual plunger stem 12 connected to and projecting from the plunger 10 and a plunger flange 14 connected to the plunger stem 12 to receive an axial pushing force to be transmitted to the plunger 10 via stem 12. A finger flange 16 surrounds the proximal end of barrel 4, and a removable needle sheath 17 covers the needle cannula to prevent an accidental needle stick. By way of example only, one such conventional syringe 2 that is suitable for use in syringe system 1 is that manufactured by Becton Dickinson Corporation having a prefilled glass barrel with a 0.4 ml fill volume.

In accordance with the present invention, the one-piece syringe system 1 also includes a syringe support and disposal jacket 18. As will soon be described, the support and disposal jacket 18 holds and positions the syringe 2 to facilitate the administration of an injection and encloses the syringe 2 following the injection to prevent reuse and facilitate the disposal thereof without subjecting health care workers to an accidental needle stick and the possible spread of disease.

The syringe support and disposal jacket 18 is preferably molded from a suitable plastic material and includes lower and upper body members 19 and 20 that are joined together by an integral living hinge 22 to permit the body members 19 and 20 to rotate relative to one another. Lower body member 19 includes an elongated, longitudinally extending recess 24 that is sized and shaped to receive the barrel 4 of syringe 2 when the syringe support and disposal jacket 18 is moved (i.e. rotated) to the syringe disposal mode (of FIGS. 4 and 5). Recess 24 terminates at an open cavity 26 through body member 19 that accepts the barrel 4 of syringe 2 therethrough in transverse alignment with body member 19 when the syringe system 1 is placed in the injection mode (of FIG. 2).

Figure 1A:
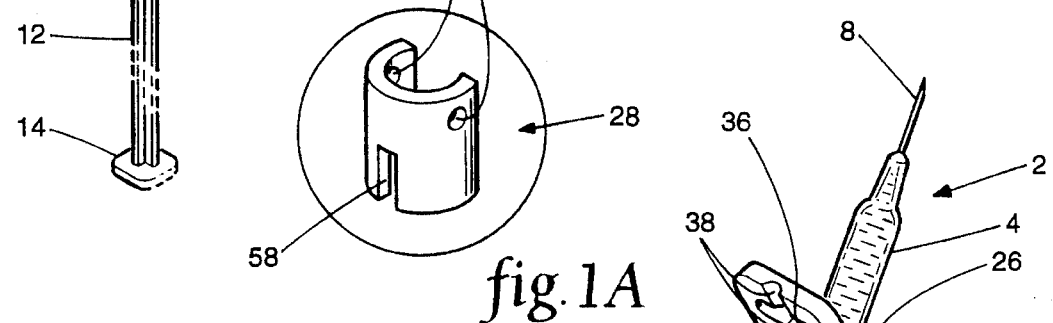
FIG. 1A is an enlarged detail taken from FIG. 1.

To this end, the syringe 2 is coupled to the syringe support and disposal jacket 18 by means of a semi-cylindrical barrel carrier 28. Barrel carrier 28 is affixed to the body member 19 and rotatable through the cavity 26 thereof by a pair of hinge pins 30 extending through pivot holes 32 (best shown in FIG. 1A). However, it is to be understood that the barrel carrier 28 may be pivotally affixed to body member 19 by integrally molded hinges (not shown), whereby the separate hinge pins 30 are avoided. In the assembled relationship, the barrel 4 of syringe 2 is snap fit into the barrel carrier 28 so that the barrel 4 can be aligned to either extend through cavity 26 during the administration of an injection or be relocated into the recess 24 of body member 19 at the conclusion of the injection.

Figure 2:
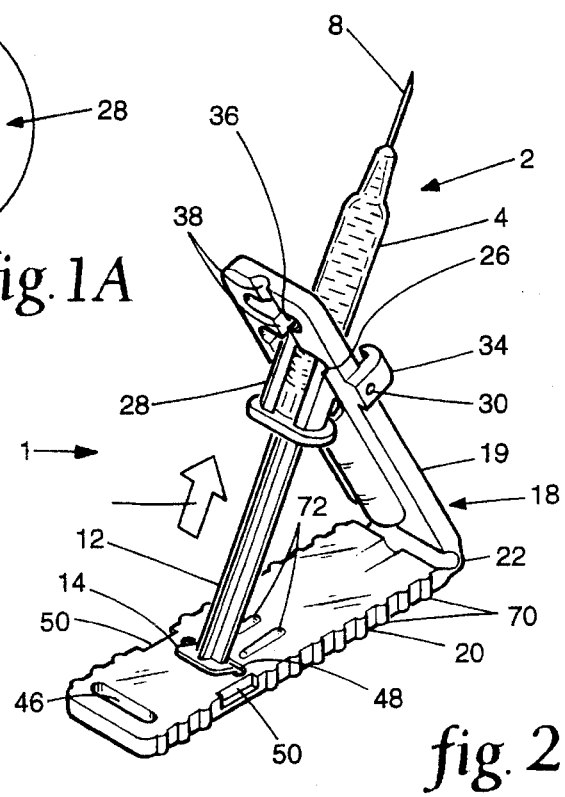
FIG. 2 is a perspective view of the one-piece syringe system of FIG. 1 in the injection mode.
Figure 3:
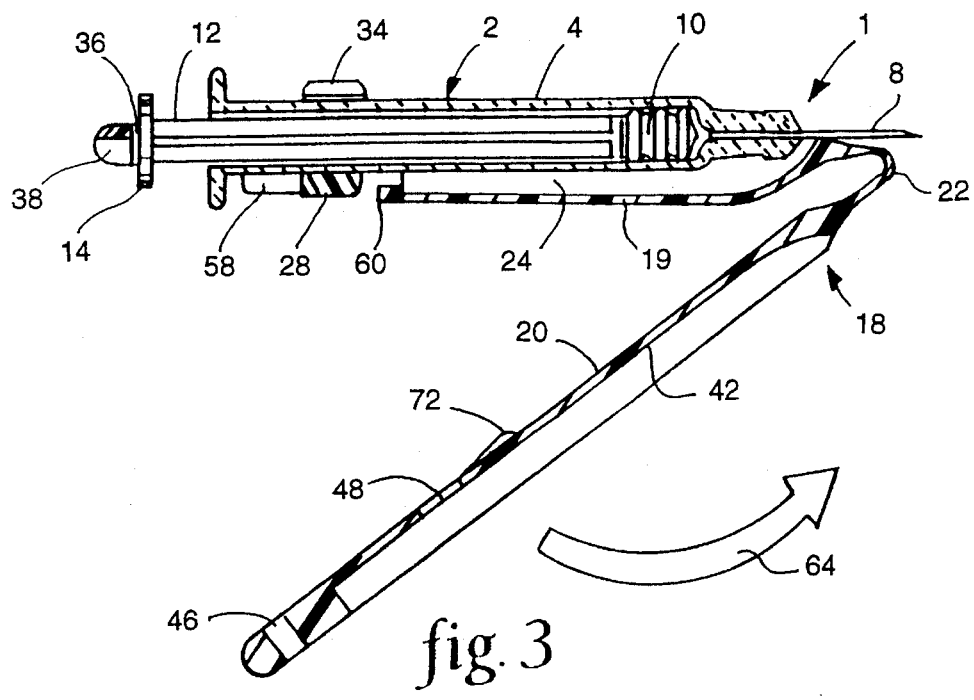
FIG. 3 is a cross-section of the one-piece syringe system moving from the injection mode to the disposal mode.
Figure 4:
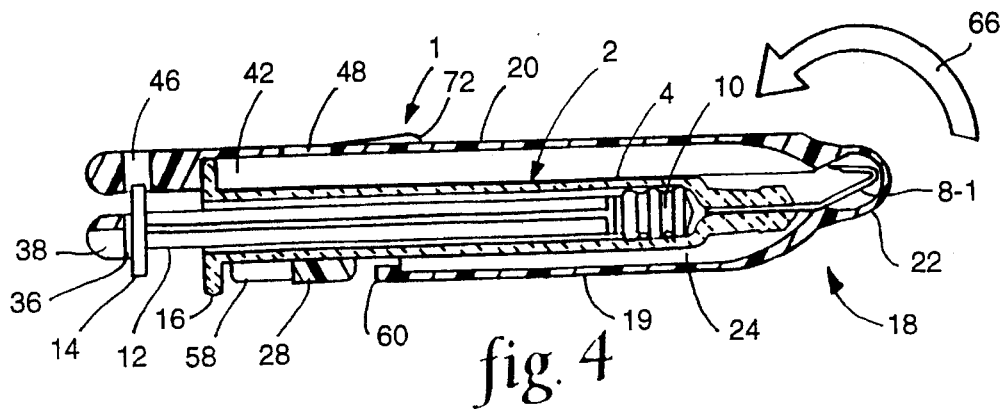
FIG. 4 is a cross-section of the one-piece syringe system in the disposal mode.
Figure 5:
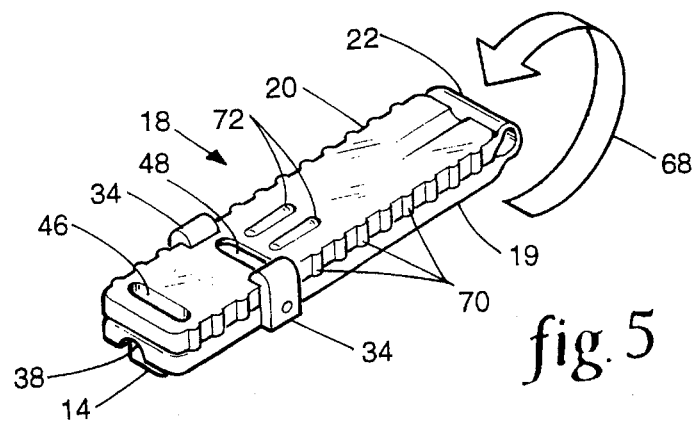
FIG. 5 is a perspective view showing the one-piece syringe system in the disposal mode.

A pair of locking tabs 34 are affixed at opposite sides of the lower body member 19 to be snapped into locking engagement with respective locking notches 50 formed in the upper body member 20 so as to reliably secure the syringe support and disposal jacket 18 in the disposal mode (best shown in FIG. 5). A plunger lock-in slot 36 is formed at a first end of lower body member 19 furthest from the hinge 22. As is best shown in FIGS. 3 and 4, the plunger flange 14 of syringe 2 is received in and retained by the lock-in slot 36 at the conclusion of the injection and when the syringe support and disposal jacket 18 is rotated about hinge 22 to the disposal mode of syringe system 1. A short, longitudinally extending channel 38 (best shown in FIG. 2) is formed in the underside at the first end of lower body member 19 to receive the plunger stem 12 connected to plunger flange 14 and projecting proximally from barrel 4 with the support and disposal jacket 18 in the aforementioned disposal mode.

The upper body member 20 of syringe support and disposal jacket 18 includes an elongated, longitudinally extending recess 42 that is sized and shaped to receive the barrel 4 of syringe 2. Thus, when the support and disposal jacket 18 is rotated to the syringe disposal mode (of FIGS. 4 and 5), the recesses 24 and 42 of lower and upper body members 19 and 20 will cooperate with one another to completely surround and enclose the barrel 4. Recess 42 terminates at a relatively wide compartment 44 in which to receive the end of syringe 2 (including finger flange 16) opposite the needle cannula 8. To accommodate the syringe 2, a plunger lock-in slot 46 is formed at a first end of the upper body member 20 farthest from the hinge 22 to receive the plunger flange 14 of plunger stem 12 at the conclusion of the injection. In this regard, when the support and disposal jacket 18 is rotated to the disposal mode (best shown in FIGS. 4 and 5), the plunger lock-in slots 36 and 46 of lower and upper body members 19 and 20 cooperate with one another to completely surround the plunger flange 14 and immobilize the plunger stem 12.

A plunger flange receptacle 48 is formed through the upper body member 20 within the compartment 44. As will be described in greater detail when referring to FIG. 2, receptacle 48 functions as a catch in which the plunger flange 14 is received and retained during the administration of an injection after the one-piece system 1 has been placed in the injection mode.

As was earlier disclosed, a pair of locking notches 50 are formed in opposite sides of the upper body member 20 to be mated with the locking tabs 32 of lower body member 19. In this regard, when the support and disposal jacket 18 is rotated to the disposal mode (best shown in FIGS. 4 and 5), the locking tabs 34 of lower body member 19 are snap fit within the locking notches 50 of upper body member 20 to reliably lock the upper and lower body members 19 and 20 together with the syringe 2 surrounded by and shielded within the package formed thereby.

Figure 6:
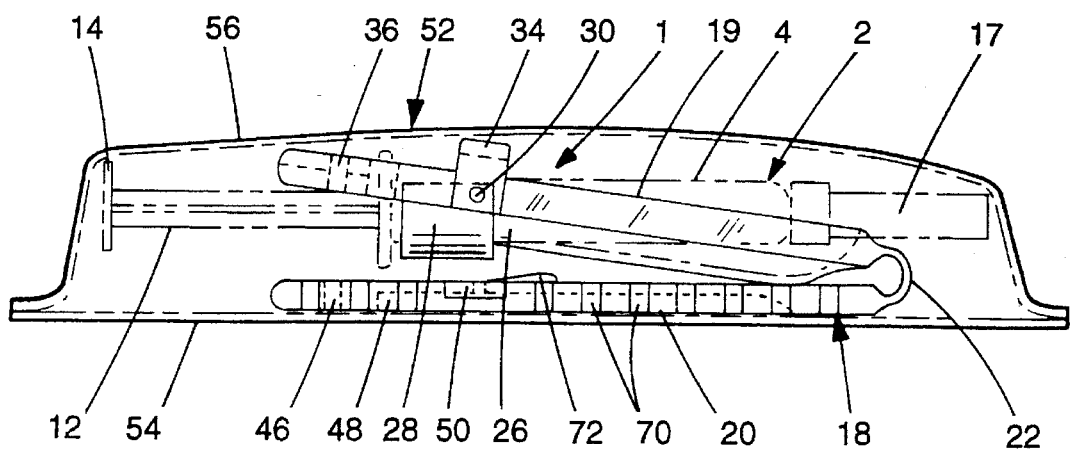
FIG. 6 is a side view showing the one-piece syringe system in the as-packaged mode.

FIG. 6 of the drawings shows the one-piece syringe system 1 in the as-packaged mode. The one-piece system 1 is suitable to be conveniently packed (for shipping and storage purposes) within a conventional blister package 52. That is, the one-piece system 1 is removably (e.g. adhesively) attached to a paper backing 54. A transparent plastic cover surrounds the system 1 and is adhesively bonded to the paper backing 54. In the as-packaged mode, the syringe 2 is in a ready-to-use configuration with the barrel 4 filled with pharmaceutical and the plunger stem 12 withdrawn proximally therefrom. The lower and upper body members 19 and 20 of syringe support and disposal jacket 18 are urged towards one another at integral hinge 22 so as to form a compact arrangement. To further minimize the space consumed by syringe system 1 within the blister package 52, the barrel carrier 28 is rotated around pivot pins 30 and moved in the cavity 26 through lower body member 19 so that the barrel 4 of syringe 2 which is coupled to barrel carrier 28 extends through cavity 26 in generally parallel alignment with the paper backing 54 of package 52. The needle sheath 17 covers the needle cannula to preserve the sterility thereof prior to use.

When it is desirable to administer an injection, the blister package 52 of FIG. 6 is opened (e.g. by tearing the cover 56 off the paper backing 54) and the one-piece syringe system 1 is removed. FIG. 2 of the drawings shows the one-piece syringe system 1 in the injection mode with the needle sheath detached from the needle cannula 8. To reach the injection mode of FIG. 2 from the as-packaged mode of FIG. 6, the lower body member 19 of syringe support and disposal jacket 18 is rotated at integral hinge 22 in a clockwise direction relative to the upper body member 20 so as to establish an angle of approximately 60 degrees therebetween. At the same time, the barrel 4 coupled to barrel carrier 28 is rotated within cavity 26 in a counter-clockwise direction until the syringe configuration of FIG. 2 is achieved.

The syringe 2 is secured in the injection mode of FIG. 2 by first locking the plunger flange 14 in the plunger flange receptacle 48 formed through the upper body member 20 of syringe support and disposal jacket 18. Next, the displacement of the barrel 4 in cavity 6 is blocked by attaching the barrel carrier 28 to the lower body member 19. More particularly, and referring briefly to FIG. 1A of the drawings, the barrel carrier 28 is shown having a detent slot 58 formed therethrough. A carriage detent 60 (best shown in FIGS. 3 and 4) extends longitudinally from lower body member 20 into the cavity 26. With the barrel carrier 28 rotated in cavity 26 to the position shown in FIG. 2, the barrel detent 60 can be located in the detent slot 58. The receipt of detent 60 in slot 58 functions as a stop to prevent the displacement of the barrel carrier 28 and the barrel 4 coupled thereto.

The injection is now administered by the health care worker exerting a pushing force against the upper body member 20 so as to cause body member 20 to move towards the lower body member 19. With the plunger flange 14 retained at plunger flange receptacle 48, the movement of body member 20 causes the plunger stem 12 (and the plunger 10 affixed thereto) to move distally through the barrel 4 in the direction of reference arrow 62 whereby to cause the pharmaceutical contents of the barrel 4 to be expulsed via the needle cannula 8 into the target tissue area (not shown).

Once the injection has been completed and the plunger stem 12 has been moved distally through the barrel 4 of syringe 2, the one-piece syringe system 1 is moved out of the injection mode of FIG. 2 and towards the disposal mode of FIGS. 4 and 5. The foregoing is achieved by first removing both the plunger flange 14 from the plunger flange receptacle 48 in body member 20 and the barrel detent 60 from the detent slot 58 in barrel carrier 28. Accordingly, the lower and upper body members 19 and 20 of syringe support and disposal jacket 18 are now free to rotate relative to one another and the barrel carrier 28 with the barrel 4 of syringe 2 coupled thereto is now free to rotate through the cavity 26 in body member 19.

To this end and referring now to FIG. 3 of the drawings, the barrel carrier 28 is rotated around hinge pins 30 in a clockwise direction so that the syringe 2 is rotated through cavity 26 until the barrel 4 is received within the recess 24 of body member 19 and the plunger flange 14 of syringe 2 is received in the plunger lock-in slot 36 of body member 19. Similarly, the portion of the plunger stem 12 projecting proximally from the barrel 4 at the conclusion of the injection is received within the longitudinal channel 38 of body member 19. However, it may be appreciated that the needle cannula 8 projects outwardly from and ahead of the recess 24 in which the barrel 4 is received. Lastly, the body member 20 is rotated at the integral hinge 22 of syringe support and disposal jacket 18 in the counter-clockwise direction represented by reference arrow 64.

FIGS. 4 and 5 of the drawings show the one-piece syringe system 1 in the disposal mode with the upper body member 20 of jacket 18 rotated above and locked to the lower body member 19 to form a compact safety disposal package. More particularly, when the upper body member 20 is moved atop lower body member 19, the recesses 24 and 42 of body members 19 and 20 completely surround and enclose the barrel 4 of syringe 2. However, the needle cannula 8 projects outwardly from and forwardly of the enclosure formed by recesses 24 and 42. Moreover, the plunger lock-in slots 36 and 46 of body members 19 and 20 completely surround and immobilize the plunger flange 14 to prevent displacement of the plunger stem 12 of syringe 2. In this same regard, when the lower and upper body members 19 and 20 of disposal jacket 18 are moved face-to-face one another with syringe 2 located therebetween, the locking tabs 34 of lower body member 19 are snap-fit within the locking notches 50 of upper body member 20. Thus, a compact disposal package is formed which may be safely handled and discarded by health care workers without the risk of an accidental needle stick.

What is more, the needle cannula 8 is rendered inaccessible and non-reusable within the disposal jacket 18. As previously described, the needle cannula projects outwardly from and forwardly of the enclosure formed by the recesses 24 and 42 in lower and upper body members 19 and 20. Therefore, when the body members 19 and 20 are rotated at the integral hinge 22 therebetween to form the disposal package of FIGS. 4 and 5, the bending of the hinge 22 (represented by the reference arrows 66 of FIG. 4 and 68 of FIG. 5), causes a corresponding bending and destruction of the cannula (designated 8-1 in FIG. 4). Thus, not only is the barrel 4 of syringe 2 locked within the disposal jacket 18, but the needle cannula 8-1 is destroyed to prevent reuse of the syringe 2 and the possible proliferation of drug abuse.

It will be apparent that while a preferred embodiment of the invention has been shown and described, various modifications and changes may be made without departing from the true spirit and scope of the invention. For example, a series of scallops or ridges 70 may be formed along the sides of either the lower or upper body member (e.g. 20) to enable the health care worker to be able to quickly and reliably locate and identify the body members 19 and 20 to facilitate the orientation and use of the syringe support and disposal jacket 18 in the injection and disposal modes. Moreover, a series of (e.g. two) short ramps 72 may be formed in the upper body member 20 adjacent the plunger flange receptacle 48 in order to guide the plunger flange 14 of the syringe 2 into the receptacle 48.

Having thus set forth the preferred embodiment of the invention, what is claimed is:

1. For a syringe including a fluid filled barrel having distal and proximal ends, a needle cannula communicating fluidically with the distal end of the barrel, and a plunger assembly located at the proximal end of the barrel and moving distally therethrough so as to expulse fluid from said barrel via said needle cannula, the improvement of a support and disposal jacket to support said syringe during the administration of an injection and to enclose and shield said syringe at the conclusion of the injection so that said syringe can be safely handled while avoiding an accidental stick from the needle cannula, said support and disposal jacket comprising:

a first body member;

a second body member;

hinge means connecting said first and second body members together so that said body members are rotatable at said hinge means;

a cavity formed completely through said first body member for receiving the barrel of said syringe therein;

carrier means detachable coupled to the barrel of said syringe in surrounding engagement therewith, said carrier means pivotally connected to said first body member so as to be rotatable in said cavity for causing a corresponding rotation of said barrel in said cavity; and a recess formed in at least one of said first or second body members and sized to receive the barrel of said syringe, said barrel rotatable from a first position extending through the cavity in said first body member in transverse alignment with said first body member at which to administer the injection to a second position in generally parallel alignment with said first body member at the conclusion of the injection, and said first and second body members being aligned with one another to form an angle when the injection is administered or being rotated at said hinge means at the conclusion of the injection until said first and second body members are aligned one atop the other with the barrel of said syringe located therebetween and in the recess of said first or second body members.

2. The support and disposal jacket recited in claim 1, wherein each of said first and second body members has a recess sized to receive the barrel of said syringe, the recesses of said first and second body members cooperating with one another at the conclusion of the injection to receive and enclose said barrel therewithin when said barrel is rotated to said second position and said first and second body members are aligned one atop the other.

3. The support and disposal jacket recited in claim 1, further comprising a detent slot formed in said carrier means and a detent projecting from said first body member into said cavity, said detent removably received by said detent slot to prevent the displacement of said carrier means and the movement of said barrel when said barrel is at said first position at which to administer the injection.

4. The support and disposal jacket recited in claim 1, further comprising at least one locking tab extending from said first body member and at least one locking notch formed in said second body member, said locking tab received in said locking notch at the conclusion of the injection when said first and second body members are aligned one atop the other to lock said first and second body members together.

5. The support and disposal jacket recited in claim 1, wherein the plunger assembly of said syringe includes a plunger stem having a plunger affixed at one end thereof and movable distally through said barrel and a plunger flange at the opposite end for receiving an axial pushing force thereagainst during the administration of the injection, said support and disposal jacket further comprising a plunger flange receptacle formed in said second body member for removably receiving said plunger flange therewithin and supporting said syringe when said barrel is at said first position, said second body member being rotated towards said first body member with said plunger flange received in said plunger flange receptacle for applying the axial pushing force to said plunger flange and thereby driving said plunger through said barrel for administering the injection.

6. The support and disposal jacket recited in claim 5, further comprising at least one ramp formed on said second body member adjacent said plunger flange receptacle for guiding the plunger flange of said plunger assembly into receipt by said plunger flange receptacle.

7. The support and disposal jacket recited in claim 5, further comprising a plunger flange lock-in slot formed in said first body member in which to receive said plunger flange when said plunger flange is removed from said plunger flange receptacle and the barrel of said syringe is rotated to said second position at the conclusion of the injection.

8. The support and disposal jacket recited in claim 7, further comprising a plunger flange lock-in slot formed in each of said first and second body members, said lock-in slots cooperating with one another at the conclusion of the injection to receive said plunger flange and thereby immobilize said plunger stem when said barrel is rotated to said second position and said first and second body members are aligned one atop the other.

9. The support and disposal jacket recited in claim 1, further comprising means to bend said needle cannula and render said cannula non-reusable when the barrel of said syringe is rotated to said second position and said first and second body members are rotated into alignment one atop the other.

10. The support and disposal jacket recited in claim 1, wherein each of said first and second body members has a pair of opposing sides, said support and disposal jacket further comprising a series of gripping ridges formed along the sides of one of said first or second body members.

11. The support and disposal jacket recited in claim 1, wherein said hinge means is a living hinge that is coextensively connected between said first and second body members.

12. The support and disposal jacket recited in claim 9, wherein the means to bend said needle cannula is said hinge means, said needle cannula being bent by said hinge means when said first and second body members are rotated one atop the other at the conclusion of the injection.

13. The support and disposal jacket recited in claim 1, wherein said carrier means detachably coupled to the barrel of said syringe is a semi-circular barrel carrier, said barrel being snap fit within said barrel carrier so as to be surrounded thereby.

14. The support and disposal jacket recited in claim 1, wherein said carrier means is hingedly connected to said first body member so as to be rotatable in said cavity formed therethrough.

15. The support and disposal jacket recited in claim 1, wherein said recess is formed in said first body member in communication with said cavity formed therethrough, the barrel of said syringe extending from said cavity to said recess when said first and second body members are rotated one atop the other at the conclusion of the injection.

* * * * *